United States Patent [19]

Brown-Skrobot et al.

[11] Patent Number: 5,547,985

[45] Date of Patent: Aug. 20, 1996

[54] ADDITIVES TO FEMININE PRODUCTS

[75] Inventors: Susan K. Brown-Skrobot, Hamilton Square; Mary R. Irving, Metuchen, both of N.J.

[73] Assignee: McNeil-PPC, Inc., Skillman, N.J.

[21] Appl. No.: 151,593

[22] Filed: Nov. 12, 1993

Related U.S. Application Data

[63] Continuation of Ser. No. 978,057, Nov. 18, 1992, abandoned, which is a continuation of Ser. No. 830,443, Feb. 3, 1992, abandoned, which is a continuation of Ser. No. 695,366, May 3, 1991, abandoned, which is a continuation-in-part of Ser. No. 605,899, Oct. 30, 1990, abandoned.

[51] Int. Cl.[6] ........................ A61K 31/22; A61K 31/225; A61K 31/23
[52] U.S. Cl. .................................... 514/546; 514/547/552
[58] Field of Search .................................. 514/546, 547, 514/552

[56] References Cited

U.S. PATENT DOCUMENTS

| | | | |
|---|---|---|---|
| 3,052,607 | 9/1962 | Hirsh | 167/82 |
| 3,219,525 | 11/1965 | Berkow et al. | 167/58 |
| 3,584,119 | 6/1971 | Langley | 424/148 |
| 3,970,759 | 7/1976 | Frankenfeld et al. | 424/343 |
| 4,022,775 | 1/1977 | Kabara | 426/532 |
| 4,067,997 | 1/1978 | Kabara | 424/312 |
| 4,113,851 | 9/1978 | Leveen et al. | 424/28 |
| 4,347,237 | 8/1982 | Evenstad et al. | 424/78 |
| 4,374,522 | 2/1983 | Olevsky | 128/285 |
| 4,393,871 | 7/1983 | Vorhauer et al. | 609/58 |
| 4,405,323 | 9/1983 | Auerbach | 604/285 |
| 4,413,986 | 11/1983 | Jacobs | 604/14 |
| 4,431,427 | 2/1984 | Lefren et al. | 604/285 |
| 4,485,029 | 11/1984 | Kato et al. | 252/106 |
| 4,551,148 | 11/1985 | Riley et al. | 604/890 |
| 4,582,717 | 4/1986 | von Bittera et al. | 427/2 |
| 4,585,792 | 4/1986 | Jacob et al. | 514/474 |
| 4,722,936 | 2/1988 | Jacob | 514/474 |
| 4,722,937 | 2/1988 | Jacob et al. | 514/474 |
| 4,769,021 | 9/1988 | Kass | 604/367 |
| 4,788,060 | 11/1988 | Endicott et al. | 424/443 |
| 4,788,180 | 11/1988 | Bloch | 514/26 |
| 4,921,694 | 5/1990 | Hoppe et al. | 424/65 |
| 4,981,686 | 1/1991 | Hardy | 424/93 |
| 4,997,851 | 3/1991 | Isaacs et al. | 514/558 |
| 5,000,749 | 3/1991 | Le Veen et al. | 604/904 |

FOREIGN PATENT DOCUMENTS

| | | |
|---|---|---|
| 1123155 | 5/1982 | Canada . |
| 1192701 | 9/1985 | Canada . |
| 0117613 | 9/1984 | European Pat. Off. . |
| 0297310 | 1/1989 | European Pat. Off. . |
| 0302836 | 2/1989 | European Pat. Off. . |
| 522M | 5/1961 | France . |
| 1307930 | 8/1962 | France . |
| 3309530C1 | 10/1984 | Germany . |
| 115016 | 2/1957 | New Zealand . |
| 183977 | 4/1979 | New Zealand . |
| 191703 | 12/1981 | New Zealand . |
| 194821 | 12/1982 | New Zealand . |
| 198139 | 7/1985 | New Zealand . |
| 209843 | 3/1987 | New Zealand . |
| 210484 | 5/1988 | New Zealand . |
| 222761 | 10/1989 | New Zealand . |
| 219973 | 5/1990 | New Zealand . |
| 221168 | 8/1990 | New Zealand . |
| 1374105 | 11/1974 | United Kingdom . |
| 2107192 | 4/1983 | United Kingdom . |
| WO86/05388 | 9/1986 | WIPO . |

OTHER PUBLICATIONS

Altenbern, *Protease Inhibitors Suppress Enterotoxin B Formation By Staphylococcus Aureus,* FEMS Microbiology Letters 3 (1978) pp. 199–202.

Ansari et al., *Sodium Bicarbonate Sodium Bicarbonate Douching for Improvement of the Postcoital Test,* Fertility and Sterility, vol. 33, No. 6, (Jun. 1980) pp. 608–612.

Flournoy et al., *The Role of Lauricidin as an Antimicrobial Agent,* Drugs of Today, vol. 21, No. 8, (1985) pp. 373–377.

Gossel, *Feminine Hygiene Products: Why Your Advice is Needed,* U.S. Pharmacist, (May 1986), pp. 20–27.

Iandolo, *Genetic Analysis of Extravellular Toxins of Staphylococcus Aureus,* Annu. Rev. Microbiol. (1989) 43: pp. 375–402.

Iandolo et al., *Regulation of Staphylococcal Enterotoxin $B^1$,* Infection and Immunity, vol. 16, No. 2 (May 1977), pp. 610–616.

Ibrahim et al., *Inhibition of Growth of Staphylococcus Aureus and Enterotoxin–A Production in Cheddar Cheese Prod. with Induced Starter Failure,* J. of Food Protec. vol. 44, No. 3, (Mar. 1981) pp. 189–193.

Kabara, *Structure–function Relationships of Surfactants as Antimicrobial Agents,* J. Soc. Cosmet. Chem., vol. 29, (Nov. 1978), pp. 733–741.

Notermans et al., *Effect of Glycerly Monolaurate on Toxin Production by Clostridium Botulinum in Meat Slurry,* J. of Food Safety vol. 3, (1981), pp. 83–88.

Orden et al., *Detect. of Staph. Enterotoxin and Toxic Shock Synd. Toxin–1 (TSST-1) by* (1991), *Immunoblot Comb. with a Semiautomated Electrophoresis System,* J. of Immuno. Meth. V. 144, pp. 197–202.

Reiser et al., *Prod. of Toxic Shock Synd. Toxin 1 by Staph. aureus Restricted to Endogenous Air in Tampons,* J. of Cl. Microb., vol. 25, No. 8, (Aug. 1987), pp. 1450–1452.

(List continued on next page.)

Primary Examiner—Kimberly Jordan

[57] ABSTRACT

Nonabsorbent products and douche compositions for cleansing and placement within the vagina contain an amount of a compound effective to inhibit the production of toxic shock syndrome toxin-1 and Enterotoxins A, B and C when the products are brought into contact with the bacteria. The products and compositions of this invention are also effective in combatting streptococcal pyrogenic exotoxin and hemolysin production by Groups A, B, F and G streptococci. The compound is selected from the group consisting of monoesters of a polyhydric aliphatic alcohol and a $C_8$–$C_{18}$ fatty acid; diesters of a polyhydric aliphatic alcohol and a $C_8$–$C_{18}$ fatty acid; and mixtures thereof. The monoesters and diesters have at least one hydroxyl group associated with their aliphatic alcohol residue.

5 Claims, No Drawings

OTHER PUBLICATIONS

Robbins et al., *Produc. of Toxic Shock Synd. Toxin 1 by Staphy. aureus as Determined by Tampon Disk–Membrane–Agar Method,* J. of Clin. Microb., V. 25, No. 8, (Aug. 1987), pp. 1446–1449.

Schlivert, *Staphy. Enterotoxi B and Toxic–Shock Synd. Toxin–1 are Significantly Assoc. with Non–Menstrual TSS,* The Lancet, May 17, 1986, vol. 1, pp. 1149–1150, (Abstract).

Schlivert et al., *Toxic Shock Synd. Staphylococcus Aureus: Effect of Tampons on Toxic Shock Synd. Toxin 1 Production,* Obstetrics & Gynecology, vol. 64, No. 5 (Nov. 1984), pp. 666–671.

Smith et al., *Enterotoxin A Synthesis in Staphylococcus aureus: Inhibition by Glycerol and Maltose,* J. of Gen. Microbiology, (1986), 132, pp. 3375–3380.

Smith et al., *Effect of Glucose Analogs on the Synthesis of Staphylococcal Enterotoxin A,* Journal of Food Safety 8, (1987), pp. 139–146.

Strobino et al., *Exposure to Contraceptive Creams, jellies and Douches and their Effect on the Zygote,* Society for Epidemiologic Research: Abstracts, pp. 434; (1985).

Tierno et al., *In vitro Amplification of Toxic Shock Syndrome Toxin–1 by Intravaginal Devices,* Contraception, vol. 31, No. 2 (Feb. 1985), pp. 185–194.

Garbe, et al., *Staphy. aureus Isolates from Patients with Nonmenstrual Toxic Shock Synd.,* JAMA, May 3, 1985, 253 (17) pp. 2538–2542.

Humphreys, et al., *Enterotoxin Production by Staphy. aureus Isolates from Cases of Septicaemia and from Healthy Carriers,* J. Med. Microbiology, Mar. 1989, 28, (3) pp. 163–172.

Crass, et al., *Involvement of Staphy. Enterotoxins in Nonmenstrual Toxic Shock Synd.,* J. Clin. Microbiol., Jun. 1986, 23, (6), pp. 1138–1139.

EPO Search Report, Application No. 90108100.0, Mar. 19, 1991.

EPO Search Report, Application No. 91118543.7, Feb. 4, 1992.

EPO Search Report, Application No. 91118572.6, Feb. 10, 1992.

ADDITIVES TO FEMININE PRODUCTS

This is a continuation of application Ser. No. 978,057, filed on Nov. 18, 1992, now abandoned, which is a continuation of Ser. No. 830,443, filed on Feb. 3, 1992, now abandoned, which is a continuation of Ser. No. 695,366 filed May 3, 1991, now abandoned, which is a continuation-in-part of application Ser. No. 605,899, filed Oct. 30, 1990, now abandoned, which hereby incorporates all subject matter set forth in all parent applications being referenced.

FIELD OF INVENTION

The present invention relates to nonabsorbent products used for intimate feminine hygiene such as douches, suppositories, gels, washes, as well as contraceptives. More particularly, the invention relates to an active component which, when incorporated into feminine hygiene products, will reduce the amount of certain toxins produced by bacteria.

BACKGROUND OF THE INVENTION

Many feminine hygiene and internal cleansing products are used by women predominantly in the form of liquids. More specifically, many women use liquid vaginal douches to irrigate and cleanse the vagina and prevent vaginal infections, for contraception and sterility and to promote abortion ("Feminine Hygiene Products: Why Your Advice Is Needed", U.S. Pharmacist, May, 1986, pp. 20–27, Thomas A. Gossel). Vaginal douche compositions may be made of a variety of compositions. Vinegar is the most common substance used for douching for the purpose of cleansing the vagina. Vinegar consists of approximately 4–6% acetic acid. There is, however, insufficient data to prove conclusively that vinegar is effective in altering the vaginal pH for a sufficient length of time to encourage growth of the normal vaginal flora, and thereby discourage infection.

British Patent Specification No. 1,374,105, published November 13, 1974 and entitled "Effervescent Compositions" describes vaginal douche compositions containing silica gel. The compositions may be tabletted and used as denture cleaners, antacids, analgesing laxatives and vaginal douches. The compositions described contain carbon dioxide and/or oxygen generating materials, e.g., persulphate/perborate mixtures, and optimum pharmaceuticals, diluents, e.g., sodium chloride, chelating agents such as EDTA, surfactants, lubricants, flavorings and odors.

U.S. Pat. No. 3,584,119, issued Jun. 8, 1971 to Daniel B. Langley, describes vaginal douche compositions which contain 3–8 pbw water soluble detergent, sodium dodecylbenzene suphonate, potassium or sodium lauryl sulphate or 2–5 pbw alkali monopersulphate or 5–10 pbw of an alkali metal borate used as aqueous solutions of 5–60 g per liter.

U.S. Pat. No. 3,219,525, issued Nov. 23, 1965 to Samuel G. Berkow et al., describes a pressurized container in which is a solution containing 1.5 to 2.5 mg of a cationic quaternary ammonium germicidal surfactant, 30–60 mg of an antiseptic wetting agent. The resultant composition is an aerosol foam.

It has been reported that when acidic or alkaline solutions were used daily to douche, there were no overall changes in the vaginal pH or the vaginal mucosa. It has also been reported, in turn, demonstrated that during the period of douching, the vaginal pH assumes that of the douche solution. Thirty minutes after douching with an acidic solution, the pH actually becomes alkaline.

Strobino et al. reported that some douches are toxic to sperm, and are therefore used as a contraceptive. In contrast, sodium bicarbonate douches are another type of douche, used to improve sperm survival and thus, to enhance fertility ("Sodium Bicarbonate Douching For Improvement Of The Postcoital Test", Fertility and Sterility, Vol. 33, No. 6, June 1980, pp. 608–612, Ansari, Gould and Ansari).

One type of illness, menstrually occurring toxic shock syndrome (TSS), a severe and sometimes fatal multi-system disease, is associated with infection or colonization by *Staphylococcus aureus* (*S. aureus*) bacteria. This disease has been linked to the use of tampons during menstruation. The disease is believed to be caused by toxic shock syndrome toxin-1 (TSST-1), the toxin produced by the majority of staphylococcal strains isolated from menstrual TSS patients.

Subsequent to the publication of reports associating toxic shock syndrome with the use of tampons, a number of investigators undertook studies designed to evaluate the effect of tampons on growth of *S. aureus* bacteria as well as the effect of tampons on the production of TSST-1 by that bacteria. Early efforts to elucidate the role of tampons in TSS yielded conflicting data. Schlievert et al. (Obstet. Gynecol., Vol. 64, pp. 666–670, November 1984) studied the effect of tampons on *S. aureus* to evaluate whether or not tampon components increase growth of *S. aureus* and production of toxic shock syndrome toxin-1. They concluded that, under the test conditions of their study, tampon components provide neither nutrients for growth of toxic shock syndrome *S. aureus* nor factors that induce production of toxic shock syndrome toxin-1 above control levels. After six hour incubation, some commercially available tampons which were tested were inhibitory to bacterial growth and suppressed toxin production. Others suppressed toxin production but did not inhibit cell growth. One tampon inhibited cell growth but increased the amount of toxin produced. On the other hand, Tierno and Hanna (Contraception, Vol. 31, pp 185–194, 1985) reported that in their experiments tampons did stimulate *S. aureus* to produce TSST-1.

Reiser et al. (J. Clin. Microbiol., Vol. 25, No. 8, pp 1450–1452, August 1987) thereafter reported the results of tests they conducted to determine the effect of four brands of tampons on production of toxic shock syndrome toxin-1. The amount of air available to the tampons which were tested was limited to that contained in sacs (made from cellulose sausage casing with a molecular weight cut-off of less than 10,000) in which the tampons were enclosed during testing. This method was deemed advantageous in that the limited amount of available air was thought to mimic more closely, than previously used methods, the in vivo condition in the vagina during menstruation with a tampon in place and in that the tampons which were tested were not altered prior to testing. The results of the tests conducted by Reiser et al. indicated that tampons provide increased surface area for the *S. aureus* bacteria to grow and adequate oxygen for toxin production. No significant inhibition of growth of the staphylococci bacteria or TSST-1 production by any of the tampons tested was noted.

Robbins et al., publishing in J. Clinical Microbiol., Vol. 25, No. 8, pp. 1446–1449, August 1987 at the same time as Reiser et al., reported the effect of 17 commercially available tampons on TSST-1 toxin production using a disk-membrane-agar (DMA) method, with incubation at 37° C. for 19 hours under 5% $CO_2$ in air. Filter membranes overlaying agar medium (with or without blood) in small petri dishes were spread inoculated with a TSST-1 producing strain of *S. aureus*. Robbins et al. concluded that the main role of tampons in TSS may be that of providing a fibrous surface for heavy colonization and sufficient air for TSST-1 production. In addition, they found evidence of inhibition of TSST-1 production by additives such as the deodorant/surfactant used in a commercially available deodorant tampon and a decrease in TSST-1 production by inhibiting growth of S. aureus as was observed in the case of a different commercially available tampon. It was thought that both inhibition of TSST-1 production and inhibition of S. aureus growth might prove to be important in reducing the risk of TSS.

S. Notermans et al. (Journal of Food Safety, Vol. 3 (1981), pages 83–88) reported that glyceryl monolaurate, when used in the proportion of 5 g per kg. of meat slurry (pH 6.0–6.2) inhibited toxin productions by *Clostridium botulinum* type A, type B and type E. This article does not mention *Staphylococcus aureus*, nor any toxins produced therefrom, nor does it mention feminine hygiene compositions using glyceryl monlaurate or toxic shock syndrome.

In toxic shock syndrome (TSS), whether associated with menstruation or not, the symptoms include fever, hypotension, rash, and desquamation of the skin. TSST-1 is highly associated with menstrual cases but is less often isolated from *Staphylococcus aureus* strains in non-menstrual cases of the illness. Since TSST-1 can induce many clinical features of TSS in the rabbit and other species, it is generally thought to be the causative toxin in TSS (Schlievert, "Staphylococcal Enterotoxin B and Toxic Shock Syndrome Toxin-1 Are Significantly Associated With Non-menstrual TSS", The Lancet, Vol. 1 (8490), May 17, 1986). However, Garbe (Garbe, Arko, Reingold et al., "*Staphylococcus aureus* isolates from patients with non-menstrual toxic shock syndrome: Evidence for additional toxins", JAMA, 1985, Vol. 253; pp. 2538–42) noted that many TSS isolates from nonmenstrual cases did not express TSST-1 though they did cause TSS-like symptoms in a rabbit model. Of the toxins formed by S. aureus nonmenstrual isolates, TSST-1 was produced by 40% of those reported by Schlievert, 1986.

The production of TSST-1 by S. aureus has predominantly been associated with menstrual TSS related to tampon usage. Experiments were initiated to determine whether one could minimize or interrupt the production of TSST-1 within absorbent fibrous materials. Unexpectedly, a group of compounds were identified which is described in copending U.S. patent applications Ser. No. 343,965, filed Apr. 27, 1989 and Ser. No. 316,742 filed Apr. 27, 1990, which are hereby incorporated herein by reference.

However, there is a need to find a douche composition which is able to combat the production of TSST-1 by *Staphylococcus aureus* within the vaginal cavity.

SUMMARY OF THE INVENTION

The invention relates to nonabsorbent compositions for irrigating the vagina containing a compound selected from the group consisting of:

a) a monoester of a polyhydric aliphatic alcohol and a fatty acid containing from eight to eighteen carbon atoms and wherein said monoester at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of the aforesaid monoesters and diesters.

The fatty acid portion of the aforementioned monoesters and diesters may be derived from caprylic, capric, lauric, myristic, palmitic and stearic acids, which are saturated fatty acids whose chain lengths, respectively, are $C_8$, $C_{10}$, $C_{12}$, $C_{14}$, $C_{16}$ and $C_{18}$. The fatty acid portion of the aforementioned monoesters and diesters may be derived as well from unsaturated fatty acids having carbon chain lengths also ranging from $C_8$ to $C_{18}$, one example of such unsaturated fatty acids being oleic acid. The preferred fatty acid for use in the practice of the present invention is lauric acid, a saturated fatty acid whose chemical formula is $C_{11}H_{23}COOH$.

As used in this specification and the appended claims, the term "aliphatic" has the meaning usually accorded it in organic chemistry, i.e. "aliphatic" refers to organic compounds characterized by straight- or branched-chain arrangement of the constituent carbon atoms.

As used in this specification and the appended claims, the term "polyhydric" refers to the presence in a chemical compound of at least two hydroxyl (OH) groups. Thus, a polyhydric aliphatic alcohol is one which has at least two hydroxyl groups and in which the carbon backbone is either straight or branched.

Polyhydric alcohols suitable for forming monoesters and/or diesters for use in the practice of the present invention are 1,2-ethanediol; 1,2,3-propanetriol (glycerol); 1,3-propanediol; 1,4-butanediol; 1,2,4-butanetriol and the like. The preferred polyhydric aliphatic alcohol for forming monoesters and diesters for use in the practice of the present invention is 1,2,3-propanetriol (commonly called glycerol) whose formula is $HOCH_2CH(OH)CH_2OH$.

The esters which are useful in the practice of the present invention have at least one hydroxyl group associated with their aliphatic alcohol residue. Thus, it will be understood that the monoester of 1,2-ethanediol and one of the aforementioned fatty acids may be used in the practice of the present invention because said ester, whose general formula is $$C_nH_{2n+1}-\underset{\underset{O}{\|}}{C}-O-CH_2-CH_2OH$$

has at least one hydroxyl group (i.e. the hydroxyl group at the far right-hand side of the structural formula shown above) in that portion of the ester derived from the aliphatic alcohol 1,2-ethanediol. On the other hand, it will be understood that the diester of 1,2-ethanediol and one of the aforementioned fatty acids cannot be used in the practice of the present invention because said ester, whose general formula is $$C_nH_{2n+1}-\underset{\underset{O}{\|}}{C}-O-CH_2-CH_2O-\underset{\underset{O}{\|}}{C}-C_nH_{2n+1}$$

does not have at least one hydroxyl group in that portion of the ester derived from the 1,2-ethanediol.

The monoester of glycerol and one of the designated fatty acids may be used in the practice of the present invention because that ester will have two hydroxyl groups associated therewith which are derived from the glycerol. The diester of glycerol and one of the designated fatty acids may also be used because that ester will have one hydroxyl group associated therewith which is derived from the aliphatic alcohol glycerol. Indeed, as will be seen hereinafter, blends of glyceryl monolaurate and glycerol dilaurate have been found to be useful in the practice of the present invention. Finally, it will be understood that the triester of glycerol and one of the designated fatty acids cannot be used in the practice of the present invention because that ester does not have at least one hydroxyl group in that portion thereof which is derived from the aliphatic alcohol, i.e. glycerol.

Preferred esters for use in the practice of the present invention are glyceryl monolaurate, glyceryl dilaurate and mixtures thereof.

Particularly preferred is glyceryl monolaurate sold under the tradename "Monomuls 90 L-12" from Henkel Corporation. This compound contains about 96% by weight glyceryl monolaurate. No glyceryl dilaurate is detected in the samples of this compound used in the Examples, below. Glyceryl monolaurate is a GRAS listed compound by in the samples of this compound used in the Examples, below. Glyceryl monolaurate is a GRAS listed compound by the FDA for use as a food emulsifier. This material is non-toxic to humans and has antimicrobial properties.

Other preferred esters for use in accordance with this invention include monolaurate derivatives of C-3 alkanols, such as 2-hydroxy-1-propyl laurate and 3-hydroxy-1-propyl laurate. Dilaurate derivatives of C-3 alkanols such as glycerol-1,3-dilaurate, glycerol-1,2-dilaurate are also expected to reduce the amount of enterotoxins A, B, C and TSST-1 with enterotoxin A produced. Ethylene glycol derivatives such as ethylene glycol monolaurate as well as polyethlyene glycol laurates, e.g., diethylene glycol monolaurate and triethylene glycol monolaurate are also expected to be active. Certain polymers are also expected to have toxin-reducing activity, for example, polyethylene glycol (200 MW) monolaurate, polyethylene glycol (400 MW) monolaurate, polyethylene glycol (1000 MW) monolaurate, and polypropylene glycol laurates such as polypropylene glycol monolaurate.

Other compounds which are believed to be active against TSST-1 toxin in the compositions of this invention are: glyceryl monocaprylate, glyceryl caprate, a mixture of glyceryl monocaprylate and glyceryl caprate, glyceryl monomyristate, glyceryl monopalmitate, glyceryl monostearate and glyceryl monooleate.

In accordance with the invention, the nonabsorbent compositions of this invention contain an amount of the above-described ester which is effective to inhibit Toxic Shock Syndrome Toxin 1 (TSST-1) when said product is exposed to *S. aureus*. For example, effective amounts have been found to be from about 0.1% and higher and, preferably, at least about 0.5% w/w of the specified mono- or diester compound (or mixtures thereof), based on the weight of the solution prepared.

Preferably, glyceryl monolaurate/glyceryl dilaurate mixtures of compounds of this invention contain at least 90% glyceryl monolaurate; more preferably, they contain at least 95% glyceryl monolaurate. Most preferably, the compound mixture should be composed substantially entirely of glyceryl monolaurate.

The active component of the compositions of this invention can be formulated into a variety of formulations such as those employed in current commercial douche formulations, or in higher viscosity douches. For example, the active component of the compositions of this invention can be formulated with surfactants, preferably nonionic surfactants, such as Cremophos RH60, Tween 20 or the like. The compositions of this invention may also contain preservatives such as methyl paraben or propyl paraben or the like. Compounds which can impart greater viscosity, such as propylene glycol, may also be added to the compositions of this invention. Generally, higher viscosity compositions are preferred in order to create formulations that will tend to remain in the vagina for a relatively long time period after administration. One sample formulation is as follows: 0.30% w/w of glyceryl monolaurate, 0.50% w/w of Cremophos RH60, 2.00% w/w Tween 20, 0.30% w/w methyl paraben, 0.10% w/w propyl paraben, 1.0% 2/2 propylene glycol, 0.04% w/w FD&C Blue #1, a dye and 95.76% w/w deionized water. Another sample formulation contains 0.50% w/w of glyceryl monolaurate, 1.50% w/w of Cremophos RH60, 1.00% w/w Tween 20, 0.30% w/w methyl paraben, 0.10% w/w propyl paraben, 0.04% w/w FD&C Blue #1, a dye and 96.56% w/w deionized water.

Glyceryl monolaurate has been described as an active ingredient useful in combatting toxic shock syndrome toxin 1 in copending U.S. patent applications Ser. No. 343,965, filed Apr. 27, 1989 and Ser. No. 316,742 filed Apr. 27, 1990, which are hereby incorporated herein by reference. These applications describe glyceryl monolaurate and its analogs as a material which, when exposed to *S. aureus* in absorbent products, can reduce formation of TSST-1 toxin. It is also believed that the active compounds in the compositions of this invention are effective in combatting the production of other types of Staphylococcal toxins, in particular, Staphylcoccal enterotoxins A, B, C and TSST-1 with A. Such effectiveness has been found with respect to these aforementioned enterotoxins when the active compound is placed on an absorbent material. The effectiveness of the compounds of the invention against the formation of Staphyloccal enterotoxins A, B, C and TSST-1 with A is described in copending United States patent applications Ser. No. 07/605, 910 (attorney docket no. PPC 369) filed Oct. 30, 1990. Glyceryl monolaurate has also been found to be effective in inhibiting the production of Streptococcal pyrogenic exotoxins (SPE) A, B and C, as well as hemolysin produced by Group A, B, F and G streptococci. It is believed that the analogs of glyceryl monolaurate will also be effective to inhibit the production of such toxins. The effectiveness of glyceryl monolaurate in inhibiting toxin production by streptococci when used in solution and in absorbent products is illustrated in copending United States patent application Ser. No. 695,366, (attorney docket no PPC 389), filed May 3, 1991.

The following examples are illustrative of the effects of the compositions of this invention upon the production of TSST-1. Of course, these examples merely illustrate the products of the invention without limiting the scope of the invention.

EXAMPLE 1

Glyceryl monolaurate was added to commercially available douches and these mixtures heated to dissolve the glyceryl monolaurate. The douche compositions were made up so as to contain glyceryl monolaurate in concentrations of 0.1, 1.0 and 10.0% by weight of the liquid douche. Specifically, Massengill Vinegar and Water Douche containing only vinegar and water was combined with glyceryl monolaurate in this Example. The solutions of this Example included Massengill Vinegar and Water Douche which is a commercially available product manufactured by Beecham Products, a division of Beecham Inc., Pittsburgh, Pa., alone and the three solutions containing Massengill Vinegar and Water Douche with 0.1% by weight glyceryl monolaurate, Massengill Vinegar and Water Douche with 1.0% by weight glyceryl monolaurate, and Massengill Vinegar and Water Douche with 10% by weight glyceryl monolaurate.

The activity of the glyceryl monolaurate was tested using the Tampon Sac Method reported by Reiser et al. in the Journal of Clinical Microbiology, Vol. 25, August 1987, pp. 1450–1452. The method was adjusted to allow for utilization of this procedure without tampons or absorbent materials as described below.

*Staphylococcus aureus* strain FRI-1169, obtained in lyophilized form from Dr. Merlin Bergdoll, Food Research Institute, University of Wisconsin, in Madison, Wis., U.S.A., was employed in the tests. A *S. aureus* suspension was prepared by thoroughly mixing one (1) milligram (mg) of the lyophilized *S. aureus* strain to one (1) milliliter (ml) of Brain Heart Infusion (BHI) Broth (obtained from Difco Laboratories, Detroit, Mich., U.S.A.), transferring said mixture into a test tube containing five (5) ml of BHI Broth, thoroughly mixing again, and incubating for twenty-four (24) hours at 37° C. prior to use.

The microorganism with media was subsequently added to sterile centrifuge tubes, spun to pellet at 2,000 r.p.m. for twenty minutes in a refrigerated centrifuge, the supernatant was decanted off, the pellet was resuspended in phosphate-buffered saline, pH 4.0. This process was repeated for five sequential 10-minute washes. The pH 4.0 solution allowed for inoculation without carry-over of nutrients and prevented the bacteria from experiencing shock on exposure to pH 4.0 solutions. This procedure was executed as described for both the Massengill and Summer's Eve Douche products.

One hundred ml of BHI agar (also obtained from Difco Laboratories) were put into each of ten 3.8 cm×20 cm culture tubes. Cellulose dialysis bags were made and sterilized in the manner reported by Reiser et al. The sterile cellulose dialysis bags (8,000 MW restrictive) were inoculated with the aforementioned *S. aureus* suspension in an amount sufficient to provide at the beginning of the test a concentration of $5.20 \times 10^8$ cfu/ml *S. aureus* bacteria.

The test solutions were prepared by adding solid glyceryl monolaurate to commercial douche solutions (Massengill and Summer's Eve), heating to 60 C in concentrations which would result in glyceryl monolaurate content of 0.1, 1.0, and 10% by weight within the heated douche solutions. These solutions were cooled while stirring and subsequently added to the inoculated dialysis bags containing *S. aureus* in 1.0 gram quantities by weight.

One gram of sterile distilled water was added to the dialysis bags inoculated with *S. aureus* alone without any additional additives and is referred to as inoculum control. Each dialysis bag or sac was then inserted into culture tubes containing the BHI agar and allowed to harden. Two inoculum controls, each in duplicate, were used. Thus, ten culture tubes were used in this test, four containing the controls (two with Massengill Vinegar and Water Douche and two without), and six culture tubes containing glyceryl monolaurate added to commercial douches in concentrations to result in Massengill Douche with 0.1% glyceryl monolaurate w/w, Massengill Douche with 1.0% glyceryl monolaurate w/w and Massengill Douche with 10% glyceryl monolaurate w/w in duplicate. After a 24-hour incubation period, the culture tubes were measured for cell concentration and TSST-1 concentration. The results of this example are set forth in Table 1.

The data shown in Table 1 demonstrate that at a concentration of 0.1% w/w glyceryl monolaurate, there is a 66% reduction in TSST-1 while at 1.0% w/w glyceryl monolaurate, a 95% reduction was observed. There was a 99% reduction in the presence of TSST-1 formation at a concentration of 10% w/w glyceryl monolaurate. The viable cell count was noted to increase in cells when exposed to Massengill Douche containing 0.1% glyceryl monolaurate from the log concentration of 7.21 in the control commercial formulation alone to an increase to 8.35. In contrast, the Massengill Douche with 1% w/w glyceryl monolaurate resulted in a log concentration of 6.85 (4.9% decrease) with the 10% w/w glyceryl monolaurate with Massengill Douche again resulting in a log concentration increase from the 7.21 seen in the control to 7.35. The methodology employed did not prevent migration of the active ingredient across the dialysis bags. However, even in light of this migration, an effect was still observed and noted.

EXAMPLE 2

The growth of, and TSST-1 production by *S. aureus* in the presence of Summer's Eve Douche with and without glyceryl monolaurate was also evaluated. Summer's Eve Douche is manufactured by C.B. Fleet Co. Inc. in Lynchburg, Va. and can be purchased commercially in the United States. Although there are several douche products sold under the trademark Summer's Eve, the product tested in this Example contained purified water, vinegar and benzoic acid. Solutions containing the Summer's Eve douche and varying concentrations of glyceryl monolaurate were heated to dissolve the active ingredient as described in Example 1. Solutions containing concentrations of glyceryl monolaurate in the amounts of 0.1, 1.0, and 10% w/w were included in this Example. The solutions were prepared and evaluated in 1.0 gram quantities as described in Example 1. The test results are reported in Table 2.

TABLE 1

THE EFFECT OF GML ADDED TO MASSENGILL DOUCHE ON TSST-1 FORMATION AND GROWTH OF *STAPHYLOCOCCUS AUREUS*

| SAMPLE | FINAL CONCENTRATION OF *S. AUREUS* ($\times 10^8$ CFU/ml) | FINAL CONCENTRATION OF *S. AUREUS*[a] ($Log_{10}$ CFU/ml) | FINAL AMOUNT TSST-1[b,c] (ng) |
|---|---|---|---|
| Inoculum Alone | 91.20 | 9.96 | 6,309.80 |
| Massengill Douche | 0.16 | 7.21 | 6,512.52 |
| Massengill Douche (0.1% GML) | 2.25 | 8.35 | 2,161.60 |
| Massengill Douche (1.0% GML) | 0.71 | 6.85 | 315.80 |
| Massengill Douche (10% GML) | 0.22 | 7.35 | 35.78 |

[a]Number of viable *S. aureus* cells expressed as log to base 10.
[b]As determined by ELISA method reported by Reiser et al. in Applied and Environmental Microbiology, December 1982, pp. 1349–1355.
[c]Mean determination of duplicate samples.

TABLE 2

THE EFFECT OF GML ADDED TO SUMMER'S EVE DOUCHE ON
TSST-1 FORMATION AND GROWTH OF *STAPHYLOCOCCUS AUREUS*

| SAMPLE | FINAL CONCENTRATION OF *S. AUREUS* ($\times 10^8$ CFU/ml) | FINAL CONCENTRATION OF *S. AUREUS*[a] ($Log_{10}$ CFU/ml) | FINAL AMOUNT TSST-1[b,c] (ng) |
|---|---|---|---|
| Inoculum Alone | 91.20 | 9.96 | 6,309.80 |
| Summer's Eve Douche (Control) | 0.021 | 6.34 | 670.94 |
| Summer's Eve Douche (0.1% GML) | 0.005 | 5.74 | 27.87 |
| Summer's Eve Douche (1.0% GML) | 0.006 | 5.83 | 4.60 |
| Summer's Eve Douche (10% GML) | 0.12 | 7.08 | 4.00 |

[a]Number of viable *S. aureus* cells expressed as log to base 10.
[b]As determined by ELISA method reported by Reiser et al. in Applied and Environmental Microbiology, December 1982, pp. 1349–1355.
[c]Mean determination of duplicate samples.

The results set forth in Table 2 show a significant reduction in both viable cell count from a log concentration of 9.96 to 6.34 (36% decrease) in the presence of the commercial douche, along with the significant reduction in TSST-1 formation, from 6,309.80 to 670.94 (89% reduction). The reduction in viable cell concentration is most likely due to the presence of benzoic acid, a known bactericide, in addition to the acetic acid in the commercial formulation. The data set forth in Table 2 resulted in a reduction in TSST-1 formation to the level of 96% less with a concentration of 0.1% glyceryl monolaurate and 99% reductions in the presence of 1.0 and 10% glyceryl monolaurate w/w as compared to that produced in the control system containing Summer's Eve Douche alone.

The presence of 0.1% w/w glyceryl monolaurate resulted in a log concentration of 5.74 (9% decrease) viable cells as compared to the control. In the presence of 1.0% w/w glyceryl monolaurate, there was a log concentration of 5.83 (8% decrease). In contrast, a 10% w/w glyceryl monolaurate solution in Summer's Eve Douche resulted in a log concentration of 7.08 (11% increase).

EXAMPLE 3

In this example, the growth of and TSST-1 production by *S. aureus* in the presence of a suspension of glyceryl monolaurate in distilled water in concentrations of 0.1, 1.0 and 10% w/w was evaluated. The solutions were evaluated in 1.0 gram quantities as described in Example 1, except that no commercial product was employed in the test. The results are set forth in Table 3.

TABLE 3

THE EFFECT OF GML SUSPENSION IN WATER ON TSST-1 FORMATION AND GROWTH OF *STAPHYLOCOCCUS AUREUS*

| SAMPLE | FINAL CONCENTRATION OF *S. AUREUS* ($\times 10^8$ CFU/ml) | FINAL CONCENTRATION OF *S. AUREUS*[a] ($Log_{10}$ CFU/ml) | FINAL AMOUNT TSST-1[b,c] (ng) |
|---|---|---|---|
| Inoculum Water (control) | 91.20 | 9.96 | 6,309.80 |
| GML (0.1%) IN WATER | 0.35 | 7.55 | 3.45 |
| GML (1.0%) in water | 0.002 | 4.31 | 2.32 |
| GML (10%) in water | 0.03 | 6.53 | 4.02 |

[a]Number of viable *S. aureus* cells expressed as log to base 10.
[b]As determined by ELISA method reported by Reiser et al. in Applied and Environmental Microbiology, December 1982, pp. 1349–1355.
[c]Mean determination of duplicate samples.

The data presented in Table 3 show a significant reduction in TSST-1 formation (99.9%) in concentrations of glyceryl monolaurate suspended in distilled water at concentrations of 0.1% w/w glyceryl monolaurate and above. Further, the one thousand-fold reduction in toxin formation also had a corresponding 99.6% reduction in *S. aureus* viable cell number noted at 0.1% w/w glyceryl monolaurate concentration. At increasing concentrations of glyceryl monolaurate, the antimicrobial effect was more predominant at the 1.0% level. There was diminished antimicrobial effect at 10% w/w glyceryl monolaurate, which could be attributed to the insolubility of the compound tested. The reductions in TSST-1 formation do not significantly change from 0.1% to 10% glyceryl monolaurate, while significant changes in viable cell numbers were noted.

EXAMPLE 4

This example was conducted to evaluate growth of, and TSST-1 production by *S. aureus* in the presence of a nonabsorbent contraceptive product, the Today Sponge, with and without glyceryl monolaurate. The Today Sponge is manufactured by Whitehall Laboratories Inc., New York, N.Y., U.S.A. The Today Sponge is described by the manufacturer as containing Nonoxynol-9, benzoic Acid, citric acid, sodium dihydrogen citrate, sodium metabisulfite, sorbic acid and water in a polyurethane foam sponge. The sponge weighs an average of 7.0 grams.

Solutions of glyceryl monolaurate in water were heated until the glyceryl monolaurate was dissolved and then pipetted onto 1.0-gram quantities of Today Sponge to result in 0.1, 1.0, and 10% w/w Glyceryl monolaurate based on the weight of the Today Sponge. The 1.0 gram samples were inserted into inoculated dialysis bags containing TSST-1-producing $S.$ $aureus$ at a concentration of $5.20 \times 10^8$ cfu/ml at the initial time. The aforementioned samples were evaluated as described in Example 1. The test results are reported in Table 4.

TABLE 4

THE EFFECT OF GML SUSPENSION IN WATER ON TSST-1 FORMATION AND GROWTH OF *STAPHYLOCOCCUS AUREUS*

| SAMPLE | FINAL CONCENTRATION OF *S. AUREUS* ($\times 10^8$ CFU/ml) | FINAL CONCENTRATION OF *S. AUREUS*[a] ($Log_{10}$ CFU/ml) | FINAL AMOUNT TSST-1[b,c] (ng) |
|---|---|---|---|
| Today Sponge (control) | 5.66 | 8.75 | 12,635.21 |
| Today Sponge (0.1% GML) | 4.60 | 8.66 | 2,185.88 |
| Today Sponge (1.0% GML) | 4.46 | 8.65 | 799.99 |
| Today Sponge (10% GML) | 0.13 | 7.13 | 3.29 |

[a]Number of viable *S. aureus* cells expressed as log to base 10.
[b]As determined by ELISA method reported by Reiser et al. in. Applied and Environmental Microbiology, December 1982, pp. 1349–1355.
[c]Mean determination of duplicate samples.

The results reported in Table 4 show a reduction in TSST-1 formation to the level of 82% less toxin with 0.1% w/w glyceryl monolaurate, 93% and 99.9% reductions noted, respectively, in the presence of 1.0 and 10% w/w of glyceryl monolaurate.

With regard to cell viability, the presence of 0.1% w/w glyceryl monolaurate resulted in a log concentration of 8.66 (1.0% decrease) as compared to the control. In the presence of 1.0% w/w glyceryl monolaurate, there was a log concentration of 8.65 (1.1% decrease), with 10% w/w glyceryl monolaurate, there was a higher antimicrobial effect, resulting in an 18% decrease in viable cells.

EXAMPLE 7

Because commercial douches are often abused as contraceptives, experimentation with glyceryl monolaurate for evaluation for spermicidal activity was undertaken. Glyceryl monolaurate was evaluated for spermicidal activity using the Sander-Cramer Test, which employs human semen. The compound was prepared in saline at a concentration of 100 mg/ml. One (1) ml of this solution was rapidly mixed with 0.2 ml of human semen. A hanging drop of this mixture was prepared and examined microscopically for sperm motility within 20 seconds from the onset of mixing. At this highest practical concentration, sperm motility lasted for more than three minutes, indicating the lack of an effect on sperm motility.

These examples demonstrate that glyceryl monolaurate is an active toxin inhibitor for TSST-1 toxin produced by *S. aureus* bacteria. Furthermore, the compound does not substantially inhibit cell growth or viability at the concentrations used in the commercial compositions of this invention. Furthermore, glyceryl monolaurate does not inhibit sperm motility.

EXAMPLE 8

In this experiment, conducted by Dr. Patrick Schlievert of the University of Minnesota, glyceryl monolaurate was added in varying concentrations to 50 ml Brain Heart Infusion Broth. These solutions were then inoculated with $1.0\times10^6$ CFU/ml of group A streptococcus strain C203 or, *S. aureus* MN8, a known TSST-1 producer. Samples containing group A streptococcus C203 were incubated at 37° C., for 12 hours, without shaking in order to reduce exposure of the organisms to oxygen, in the presence of 7% $CO_2$. Samples containing MN8 were incubated comparably except with shaking (at a rate of 200 RPM) and in a standard incubator. The results of this experiment are summarized in Table 5.

TABLE 5

THE EFFECT OF GLYCERYL MONOLAURATE ON TOXIN PRODUCTION AND CELL VIABILITY OF GROUP A STREPTOCOCCUS AND *S. AUREUS* MN8

| Sample | GML mg/100 | CFU | SPE type A | SPE type B | TSST-1 |
|---|---|---|---|---|---|
| C203 | 0 | $3.1 \times 10^8$ | 6.0 | 3.0 | |
| | 0.05 | $3.5 \times 10^8$ | 6.0 | 3.0 | |
| | 0.1 | $3.2 \times 10^8$ | 1.5 | 0.75 | |
| | 0.25 | $3.3 \times 10^8$ | N.D. | N.D. | |
| | 0.5 | $3.2 \times 10^8$ | N.D. | N.D. | |
| | 0.75 | $2.0 \times 10^8$ | N.D. | N.D. | |
| | 1.0 | $4.0 \times 10^7$ | N.D. | N.D. | |
| | 1.25 | $3.5 \times 10^6$ | N.D. | N.D. | |
| | 1.50 | 0 | N.D. | N.D. | |
| | 1.75 | 0 | N.D. | N.D. | |
| | 2.0 | 0 | N.D. | N.D. | |
| | 5.0 | 0 | N.D. | N.D. | |
| | 10.0 | 0 | N.D. | N.D. | |
| MN8 | 0 | $8.4 \times 10^9$ | | | 48 |
| | 0.05 | $9.0 \times 10^9$ | | | 48 |
| | 0.1 | $9.4 \times 10^9$ | | | 48 |
| | 0.25 | $6.2 \times 10^9$ | | | 12 |
| | 0.5 | $1.8 \times 10^{10}$ | | | N.D. |
| | .75 | $9.7 \times 10^9$ | | | N.D. |
| | 1.0 | $2.1 \times 10^{10}$ | | | N.D. |
| | 1.25 | $7.0 \times 10^9$ | | | N.D. |
| | 1.5 | $1.4 \times 10^{10}$ | | | N.D. |
| | 1.75 | $1.1 \times 10^{10}$ | | | N.D. |
| | 2.0 | $4.0 \times 10^5$ | | | N.D. |
| | 2.25 | $2.0 \times 10^5$ | | | N.D. |
| | 2.5 | $2.3 \times 10^4$ | | | N.D. |

TABLE 5-continued THE EFFECT OF GLYCERYL MONOLAURATE ON
TOXIN PRODUCTION AND CELL VIABILITY OF
GROUP A STREPTOCOCCUS AND S. AUREUS MN8

| Sample | GML mg/100 | CFU | SPE type A | B | TSST-1 |
|---|---|---|---|---|---|
|  | 5.0 | $2.1 \times 10^4$ |  |  | N.D. |
|  | 10.0 | $2.9 \times 10^4$ |  |  | N.D. |

EXAMPLE 9

In this example, conducted by Dr. Patrick Schlievert, group A streptococcal strains, individually expressing SPEA, SPEB or SPEC and strains from groups B, F and G streptococci were evaluated for the effect of glyceryl monolaurate on production of exotoxin. Using the method set forth in Example 8, microorganisms were exposed to varying concentrations of glyceryl monolaurate in a Brain Heart Infusion broth. Strain 594, which produces SPEA, Strain 86-858, which produces SPEB and strain T18P, which produces SPEC toxins respectively, were used. Toxin production was measured by Western immunoblotting for periods up to 96 hours. The results of this experiment to determine the effect of glyceryl monolaurate on production of SPEA, SPEB and SPEC toxins are set forth in Table 6.

S. aureus strain Mn8 was also exposed to glyceryl monolaurate. The amount of TSST-1 production by S. aureus strain Mn8 was measured. The results of this test are set forth in Table 7.

Streptolysins O and S, also produced by strains 594, 86–858 and T18P, as well as Group B streptococcal hemolysin, Group F streptococcal hemolysin and Group G streptococcal hemolysin were measured by lysis of 0.1% sheep erythrocytes and 0.014% 2-mercaptoethanol as a reducing agent performed in 0.75% agarose in phosphate buffer solution (PBS), 4.5 ml/slide. The PBS was composed of 0.005 Molar sodium phosphate, with 0.15 Molar NaCl at pH 7.0. Hemolysis induced by 20 ul cell free culture added to wells punched in slides after 24 hours was used as a measure of hemolysin production. Lipase was measured in the same way as hemolysin, except that clearing of 0.1% tributyrin was used as the standard.

Results of reduced streptolysin O and S are also set forth in Table 6. The results of the experiments demonstrate the effect of glyceryl monolaurate on toxin production by Groups B, F and G streptococci in Tables 8, 9, and 10, respectively. The data show a marked reduction in the amounts of toxin and/or hemolysin produced by Groups A, B, F and G streptococci in the presence of glyceryl monolaurate.

TABLE 6

EFFECT OF GLYCERYL MONOLAURATE
ON GROUP A STREPTOCOCCI

| Bacterium[a] | GML (μg/ml) | Log CFU/ml | SPE (μg/ml) | Reduced Hemolysin[b] |
|---|---|---|---|---|
| 594 (SPEA) | 0 | 8.6 | 3.2 | 7.0 |
|  | 2.5 | 8.5 | 0.3 | 4.0 |
|  | 10.0 | 8.3 | 0.3 | 0.0 |
|  | 20.0 | 6.0 | 0.0 | 0.0 |
| 86-858 (SPEB) | 0 | 8.0 | 0.8 | 4.0 |
|  | 2.5 | 7.7 | 0.0 | 2.0 |
|  | 10.0 | 7.7 | 0.0 | 0.0 |
|  | 20.0 | 5.8 | 0.0 | 0.0 |
| T18P (SPEC) | 0 | 7.9 | 0.4 | 8.0 |
|  | 2.5 | 7.9 | 0.0 | 8.0 |
|  | 10.0 | 6.1 | 0.0 | 0.0 |

[a] Inoculum size between $10^5$ and $10^6$ CFU/ml
[b] Includes streptolysin O and S measured in mm diameter of lysis

TABLE 7

EFFECT OF GML ON Staphylococcus aureus[a] MN8

| | 4 hr | | | | 8 hr | | | | 24 hr | | | | 48 hr | | | | 96 hr | | | |
|---|---|---|---|---|---|---|---|---|---|---|---|---|---|---|---|---|---|---|---|---|
| GML (μg/ml) | Log cells ml | L[b] | H[c] | T[d] | Log cells ml | L | H | T | Log cells ml | L | H | T | Log cells ml | L | H | T | Log cells ml | L | H | T |
| 0 | 6.8 | 2 | 0 | 0 | 9.0 | 10 | 9 | 2 | 10.2 | 15 | 15 | 40 | 10.2 | 15 | 15 | 40 | 10.3 | 15 | 16 | 40 |
| 20 | 5.8 | 2 | 0 | 0 | 7.5 | 6 | 0 | 0 | 10.0 | 15 | 13 | 16 | 10.3 | 14 | 5 | 40 | 10.3 | 15 | 16 | 40 |
| 100 | 5.8 | 2 | 0 | 0 | 6.3 | 6 | 0 | 0 | 8.3 | 8 | 0 | 0 | 10.0 | 13 | 4 | 8 | 10.3 | 15 | 8 | 16 |
| 300 | 5.6 | 2 | 0 | 0 | 5.8 | 2 | 0 | 0 | 6.9 | 4 | 0 | 0 | 7.0 | 6 | 0 | 0 | 10.3 | 15 | 2 | 8 |

[a] Inoculum size $1.0 \times 10^5$/ml
[b] L, Lipase mm
[c] H, Hemolysin mm lysis Rabbit RBC
[d] T, TSST-1 (μg/ml)

TABLE 8

EFFECT OF GML ON GROUP B STREPTOCOCCUS

| | 8 hr | | 24 hr | |
|---|---|---|---|---|
| GML (μg/ml) | Log cells/ml | Hemolysin | Log cells/ml | Hemolysin |
| 0 | 8.7 | 2 | 8.5 | 2 |
| 2.5 | 8.1 | 0 | 8.4 | 0 |
| 10.0 | <4.0 | 0 | <3.0 | 0 |

Inoculum size $2.0 \times 10^5$/ml

TABLE 9

| EFFECT OF GML ON GROUP F STREPTOCOCCUS | | | | |
|---|---|---|---|---|
| | Amount of Time: | | | |
| GML | 8 hr | | 24 hr | |
| (μg/ml) | Log cells/ml | Hemolysin | Log cells/ml | Hemolysin |
| 10 | 8.3 | 7 | 8.3 | 7 |
| 2.5 | 8.5 | 0 | 8.3 | 0 |
| 10.0 | $<10^4$ | 0 | $<10^3$ | 0 |

Inoculum size $2.0 \times 10^5$/ml

TABLE 10

| EFFECT OF GML ON GROUP G STREPTOCOCCUS | | | | |
|---|---|---|---|---|
| | Amount of Time: | | | |
| GML | 8 hr | | 24 hr | |
| (μg/ml) | Log cells/ml | Hemolysin | Log cells/ml | Hemolysin |
| 0 | 8.9 | 8 | 10.0 | 8 |
| 2.5 | 8.1 | 5 | 10.0 | 6 |
| 10.0 | $<10^4$ | 0 | $<10^3$ | 0 |

Inoculum size $8 \times 10^5$/ml

EXAMPLE 10

In this experiment, conducted by Dr. Patrick Schlievert, attempts were made to induce streptococcal strain C203 and staphylococcal strain MN8 to grow on plates containing glyceryl monolaurate. The minimum inhibitory concentration of glyceryl monolaurate for strain C203 was 1 mg/100 ml on the agar plates when $5\times10^6$ CFU were plated. The 2 mg/100 ml plate contained no growth. The minimum inhibitory concentration of glyceryl monolaurate for strain MN8 was 5 mg/100 ml when $7\times10^8$ CFU were plated. The 7.5 mg/100 ml plate contained no growth. This experiment was attempted on an average of twice per week for a period of six months. The data indicate that no mutants are able to grow in the presence of inhibitory levels of glyceryl monolaurate.

What is claimed is:

1. A method of inhibiting the production of toxic shock syndrome toxin-1 comprising exposing toxic shock syndrome toxin-1 producing *Staphylococcus aureus* bacteria to an absorbent product comprising a pharmaceutically acceptable carrier and a compound selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters, said compound being present in an amount which is effective to inhibit the production of toxic shock syndrome toxin-1 by *Staphylococcus aureus* bacteria when said product is exposed to said bacteria.

2. A method according to claim 1 wherein said composition is a vaginal cleansing composition.

3. A method according to claim 1 wherein said fatty acid is lauric acid.

4. A method according to claim 1 wherein said polyhydric alcohol is glycerol.

5. A method according to claim 1 wherein said compound is glyceryl monolaurate.

* * * * *